United States Patent [19]

Harris

[11] Patent Number: 5,799,650
[45] Date of Patent: Sep. 1, 1998

[54] FEMORAL COMPRESSION DEVICE AND METHOD

[76] Inventor: Scott M. Harris, 42 Castle Dr., Sharon, Mass. 02067

[21] Appl. No.: 826,222

[22] Filed: Mar. 27, 1997

[51] Int. Cl.$^6$ ............................................. A61F 5/24
[52] U.S. Cl. .................... 128/96.1; 128/107.1; 128/869; 128/882
[58] Field of Search ................... 128/95.1, 96.1, 128/98.1, 99.1, 100.1, 102.1, 104.1, 106.1, 107.1, 115.1, 845, 846, 869, 882; 602/19

[56] References Cited

U.S. PATENT DOCUMENTS

| | | | |
|---|---|---|---|
| 1,562,935 | 11/1925 | Whisner | 602/19 |
| 2,753,864 | 7/1956 | Weidemann | 602/23 |
| 4,481,941 | 11/1984 | Rolfes | 602/19 |
| 4,829,994 | 5/1989 | Kurth . | |
| 4,957,105 | 9/1990 | Kurth . | |
| 4,977,893 | 12/1990 | Hunt . | |
| 5,263,966 | 11/1993 | Daneshvar . | |
| 5,307,811 | 5/1994 | Sigwart et al. . | |
| 5,383,893 | 1/1995 | Daneshvar . | |
| 5,423,852 | 6/1995 | Daneshvar . | |
| 5,514,155 | 5/1996 | Daneshvar . | |
| 5,620,412 | 4/1997 | Modglin | 602/19 |

*Primary Examiner*—Michael A. Brown
*Attorney, Agent, or Firm*—McCormick, Paulding & Huber

[57] ABSTRACT

A femoral compression device for preventing post-catheterization wound bleeding includes a rigid restraining member strapped in fixed position to a patient to prevent hip flexion. A compression strap connected to the restraining member urges a discrete compression element toward the wound site. The compression strap cooperates with the discrete compression element to form a general ball and socket joint therebetween, whereby slight movement of the compression strap relative to the compression element will not cause a corresponding movement of the compression element.

26 Claims, 2 Drawing Sheets

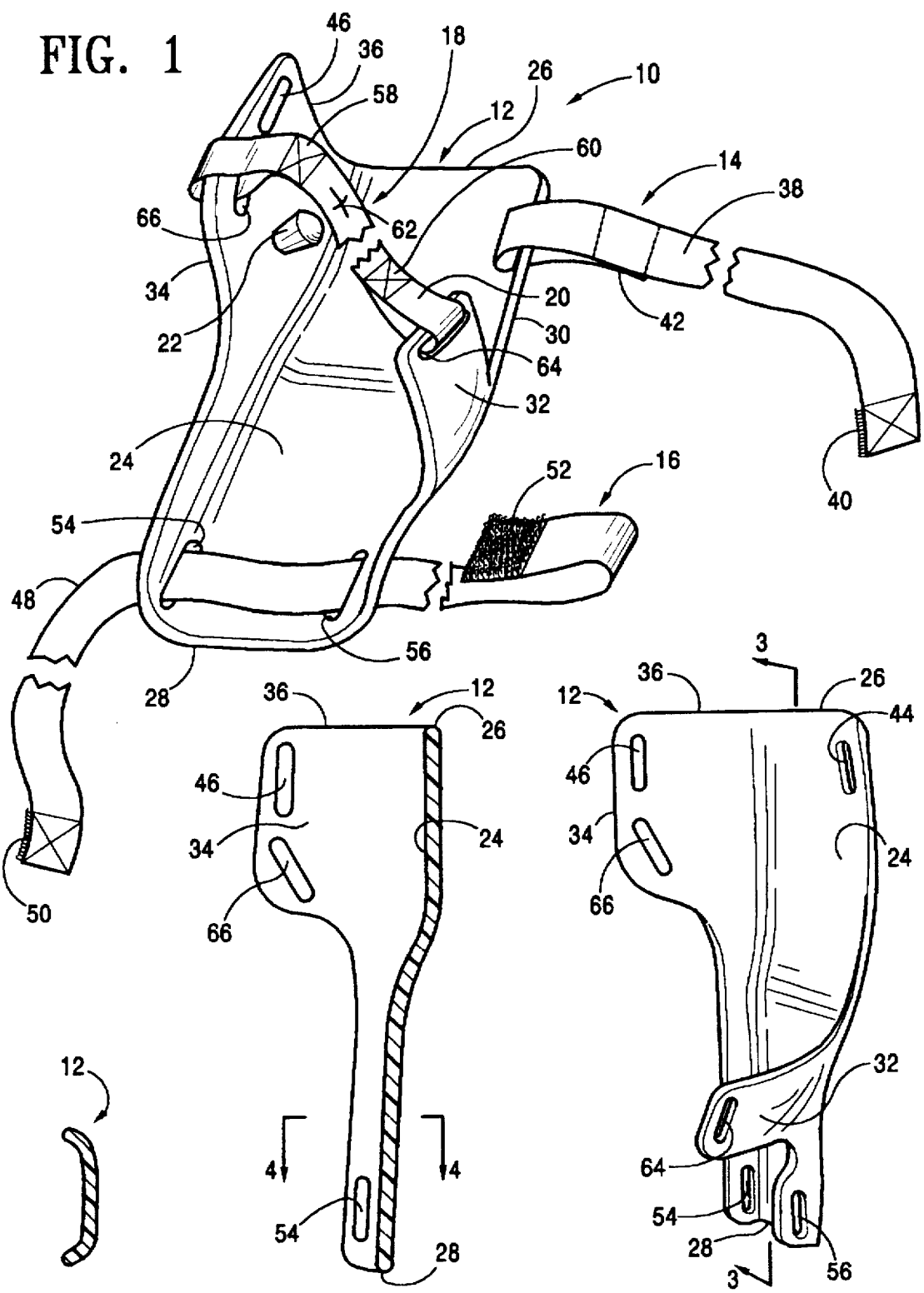

5,799,650

FEMORAL COMPRESSION DEVICE AND METHOD

BACKGROUND OF THE INVENTION

This invention relates in general to surgical devices and deals more particularly with an improved femoral compression device for preventing post-catheterization wound bleeding. The purpose of the present device is to exert compressive force over a femoral artery and possibly vein catheter puncture site. Bleeding from the site has been a problem for catheterization teams and angiographers, because of the size of the catheters used and the fact that many patients who undergo such procedure receive anticoagulants.

A rather common but somewhat primitive procedure for controlling post-catheterization bleeding involves the use of a sandbag positioned in the wound area over a pressure bandage. This procedure is not particularly satisfactory, because the magnitude of the pressure applied to the wound area cannot be easily controlled. Further, the procedure is quite uncomfortable for the patient, because it requires that the patient remain substantially motionless to avoid shifting or dislocation of the sandbag.

Various external pressure application devices have been heretofore provided for preventing post-catheterization wound bleeding and examples of such devices are found in patents hereinafter briefly discussed.

U.S. Pat. Nos. 4,957,105 and 4,829,994 to Kurth are directed to a femoral arterial or venous compressive device which includes a flexible pelvic apron hung from the hip points of the pelvis by hip straps. A shaped mass or pellet attached to the underside of the apron over the incision site of the femoral vessel is forced toward the incision site by the tourniquet action of an elastically extensible groin strap attached to front and rear parts of the pelvic apron in proximity to the shaped mass and drawn tightly through the groin.

Four recent patents to Daneshvar, U.S. Pat. Nos. 5,263,996; 5,383,893; 5,423,852 and 5,514,155 relate to the use of an inflatable balloon in devices for applying pressure to prevent post-catheterization wound bleeding and disclose various arrangements of flexible wraps and straps to permit application of pressure by an inflatable balloon.

The patent to Sigwart, U.S. Pat. No. 5,307,811 discloses a substantially rigid adjustable base plate which carries a pressurizing element for exerting compressive force against a patient's body at a femoral artery puncture site. The base plate is secured over the femoral puncture site of a treated patient by a flexible belt extending around the body of the patient at the hip area.

While the devices hereinbefore generally discussed allow for varying degrees of patient movement, such devices generally require some form of compression strap extending across the groin region. Any substantial degree of hip flexion which may result in shifting of the compression strap is likely to cause substantial loss of arterial compression. Consequently, it seems probable that such devices will require frequent monitoring and adjustment to maintain desired pressure.

Accordingly, it is the general aim of the present invention to provide an improved femoral compression device which stabilizes the pelvis with respect to a compressing means for applying external compressive force at an arterial or venous wound site to enable a patient to move from side to side without substantial risk of shifting the compressing means with resulting loss of compression.

SUMMARY OF THE INVENTION

In accordance with the present invention, an improved femoral compression device has restraining means for limiting hip flexion which includes a substantially rigid restraining member and attaching means for securing the restraining member in a substantially fixed generally predetermined position on a patient's body, and adjustable compressing means carried by the restraining means for applying external pressure to and maintaining pressure at a femoral artery or vein puncture site.

BRIEF DESCRIPTION OF THE DRAWINGS

FIG. 1 is an exploded fragmentary perspective view of a femoral compression device embodying the present invention.

FIG. 2 is a perspective view of the restraining member shown with the attaching and compressing straps removed therefrom.

FIG. 3 is a somewhat reduced fragmentary sectional view taken along the line 3—3 of FIG. 2.

FIG. 4 is a sectional view taken along the line 4—4 of FIG. 3.

DETAILED DESCRIPTION OF PREFERRED EMBODIMENT

Figure 5:
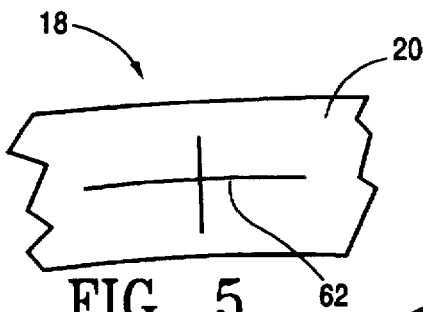
FIG. 5 is a fragmentary plan view of the compression strap.

Turning now to the drawings, a femoral compression device embodying the present invention and shown in FIG. 1 is indicated generally by the reference numeral 10. The illustrated device 10 is particularly adapted to be secured to and worn by a patient in a supine position to prevent post-catheterization wound bleeding and essentially comprises a substantially rigid restraining member, indicated generally at 12, and a plurality of attaching strap assemblies for releasably securing the restraining member 12 in a generally predetermined position relative to the patients body and which include upper and lower strap assemblies indicated generally at 14 and 16. The device 10 further includes and adjustable compressing assembly indicated generally at 18 and which includes an adjustable compression strap 20 and a discrete compression element, designated generally by the numeral 22, for positioning relative to the compression strap to cooperate with the latter strap and apply external pressure to and maintain pressure upon a femoral artery or vein puncture site, all of which will be hereinafter further discussed.

Considering now the restraining member in further detail and referring again to FIG. 1 and also to FIGS. 2–4, the illustrated restraining member 12 comprises a generally anatomically contoured shell having a substantially uniform wall thickness and molded or otherwise formed from a resilient durable light weight plastic material, polypropylene being presently preferred for this purpose. The illustrated restraining member 12 is right handed, being adapted to overlie a right posterior portion of a patient's body, since most catheterization procedures are performed in the right inguinal region. However, it should be understood that the device may also be made of opposite hand and such modified forms of the device are contemplated within the scope of the present invention. The restraining member 12 is also sized to generally match a patient's body requirements. It is presently anticipated that production of the device in three sizes will generally satisfy most surgical needs.

Considering further the restraining member 12 as it appears oriented in FIGS. 1–4 and with particular reference to its generally predetermined position relative to a typical patient's body, the restraining member 12 has an elongated longitudinally vertically disposed frontal surface 24 which extends downwardly from a transversely extending upper edge 26, which edge adapted to be positioned proximate the pelvic brim. The frontal surface terminates at a transversely extending lower edge 28, the latter edge being adapted to be located proximate the patient's mid thigh. The upper portion of the frontal surface 24 is rearwardly offset relative to the lower portion thereof to accommodate the right cheek of the patient's buttocks. This offset surface arrangement allows the lower portion of the frontal surface 24 to overly an associated posterior portion of the right thigh. The inner edge of the restraining member 12, indicated at 30, has an upper portion adapted to be disposed proximate and generally in parallel alignment with the midline of the body and the buttocks crease. The lower portion of the restraining member 12 is somewhat narrower than the upper portion and is anatomically contoured to generally complement the posterior portion of the thigh. A first strap connecting portion 32 at the inner side of the restraining member 12 projects forwardly beyond the frontal surface 24 for positioning within the patient's crotch region. A second strap retaining portion 34 at the upper outer side portion of the restraining member 12 projects forwardly beyond the frontal surface of the member and is partially defined by an upper edge 36 adapted to be disposed proximate the iliac crest.

A plurality of slots are formed in and extend throughout the retaining member 12 for receiving the various attaching straps for securing the device to the patient and the compression strap for applying pressure at the wound site, as will be hereinafter further discussed.

The strap assemblies used in practicing the invention may be made from any suitable material and may take various forms. However, the presently preferred straps are connected to the restraining member 12 and joined to each other by VELCRO or a similar mating J-hook and loop fastening material.

In accordance with presently preferred construction the straps used in practicing the invention are fabricated from fastener loop material and carry patches of mating J-hook material. Thus, a patch of J-hook material carried by a strap may be releasably connected to that strap at substantially any position along the length of the strap. This strap connecting arrangement permits rapid connection and separation of the various straps while affording a substantially infinite range of strap adjustability.

In the illustrated embodiment 10, the upper strap assembly 14 preferably comprises a single strap 38 fabricated from loop material, as hereinbefore discussed, and having patches of J-hook material 40 and 42 at its opposite ends. A looped end of the strap 38 (FIG. 1) passes through a slot 44 formed in the inner marginal portion of the restraining member 12 near the upper edge and shown in FIG. 2. The opposite end of the strap which carries the patch 40 preferably remains free until the device is attached to a patient. This arrangement of the upper strap assembly 14 is preferred, because the connected end portion of the strap will normally be inaccessible, being located beneath the patient when the device is secured to the patient in supine position. A slot 46 formed in the second connecting portion 34 near the upper edge 46 receives the free end portion of the strap 14 when the device is secured to the patient.

The lower connecting strap assembly 16 includes a strap 48 and J-hook patches 50 and 52. It is of similar construction to the upper strap assembly 14 but of a somewhat shorter length. The lower strap 48 is preferably threaded through opposing slots 54 and 56 formed in opposite side marginal portions of the restraining member 12 and located near the lower edge 28.

Considering now the preferred compressing assembly 18 which comprises the adjustable compression strap 20 and the discrete compression element 22 which cooperates with the latter strap. The strap 20 is similar in most respects to the upper and lower attaching straps previously described in that it is preferably fabricated from loop material and has J-hook patches 58 and 60 at its opposite ends. However, unlike the previously described straps the strap 20 has a cruciform slit 62 extending through it as best shown in FIG. 5 and for a purpose which will be hereinafter further evident. The strap 20 is connected to the restraining member 12 by threading the strap through slots 64 and 66 formed in the first and second connecting portions 32 and 34, respectively, and looping the ends of the strap to connect the J-hook 58 and 60 to associated portions of the strap 20, substantially as shown in FIG. 1. However, the strap 20 is preferably positioned on and connected to the restraining member 12 after the restraining member has been secured to the patient, as hereinafter further discussed.

Figure 7:
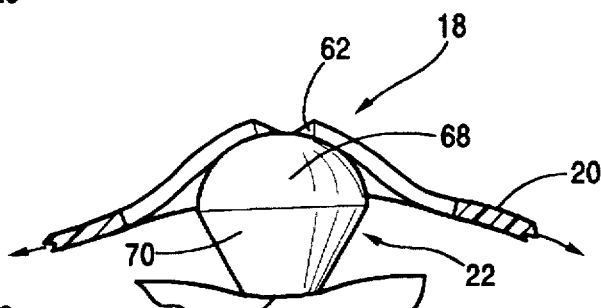
FIG. 7 is a somewhat enlarged fragmentary sectional view taken along the line 7—7 of FIG. 6 and showing the compression element in a compressing position.
Figure 6:
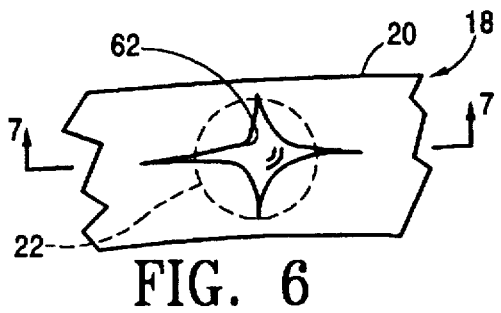
FIG. 6 is similar to FIG. 5 but shows the compression strap in compressing engagement with the compression element.
Figure 8:
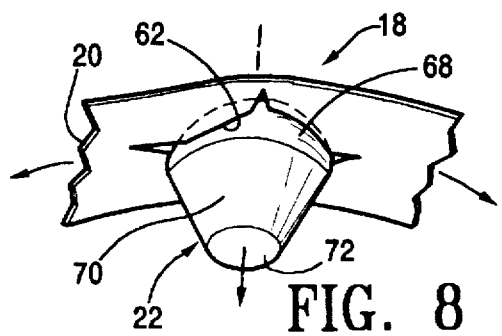
FIG. 8 is a fragmentary perspective view showing the underside of the compression strap and compression element shown in FIGS. 6 and 7.

Referring now particularly to FIGS. 6–8 the discrete compression member 22 may be formed from any suitable material, but preferably, and as shown, it is molded from a durable plastic material and has a parti-spherical head portion 68 and a frustoconical portion 70 which forms a junction with the head portion 68 and axially converges in a direction away from the head portion. The free end of the frustoconical portion defines a generally circular pressure surface 72 for applying pressure at a wound site, as will be hereinafter further described.

Figure 9:
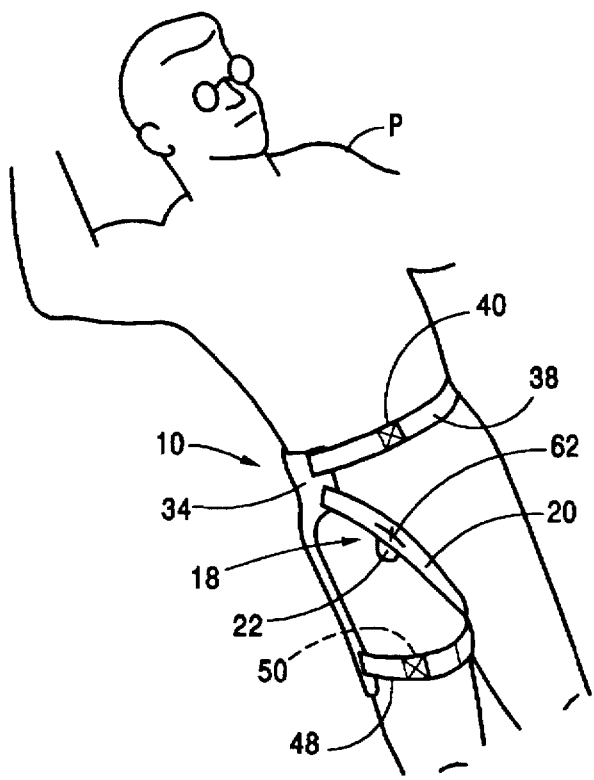
FIG. 9 is a fragmentary sectional view showing the femoral compression device of FIG. 1 in an arterial compressing position on a patient shown in supine position.
Figure 10:
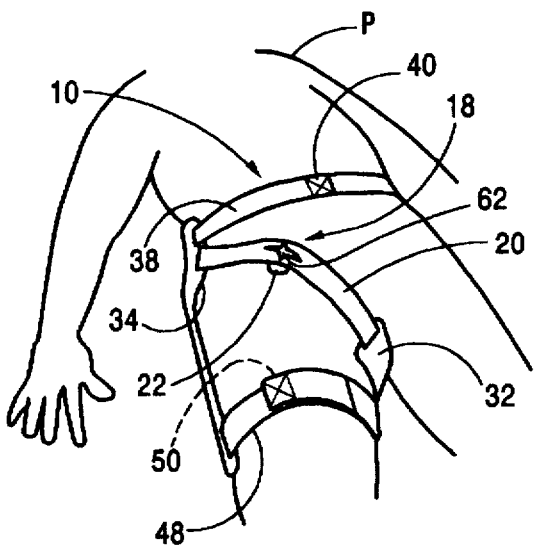
FIG. 10 is another perspective view of the patient shown in FIG. 9.

In FIGS. 9 and 10 the illustrated device 10 is secured to a patient P shown in a supine position. Preparatory to securing the device to the patient P one end of the compression strap 20 may be attached to an associated one of the connecting portions 32 and 34 for convenience. The restraining member 12 is positioned posteriorly of the patient in a predetermined position relative to the patient's body, as hereinbefore generally described. Thereafter, the upper attaching strap 38 is extended across the patient's abdomen and the free end of the strap is inserted through the inner side of the slot 46, looped back across the patient's abdomen and tensioned to a snug position, after which the J-hook patch 40 at the free end of the strap is brought into gripping engagement with an associated portion of the loop material which comprises the strap 14.

The lower strap 48 is attached to the thigh by bringing the inner end portion of the strap across the anterior surface at mid thigh to expose the J-hook patch 52 in a forwardly facing direction proximate the mid-line of the leg. The J-hook portion 52 is held in the latter position while the other end of the strap is drawn snugly into position overlying the J-hook patch 52 and joined thereto. Thereafter, the free outer end portion of the strap 48 may be looped back onto the strap and attached thereto by J-hook patch 50, whereby the unused free end of the lower strap 48 is secured.

After the restraining member 12 has been secured in its proper predetermined position relative to the patient's body to limit hip flexion, that is a forward raising of the leg by hip movement, the compression assembly 18 is adjusted and secured to apply and maintain pressure at the wound site. After the free ends of the strap 20 have been threaded through respectively associated slots 64 and 66 in the first and second connecting portions 32 and 34 the position of the strap 20 is adjusted relative to the restraining member to align the cruciform slit 62 with a preselected pressure point in the ingrinal region where pressure is to be applied. The pressure element 22 is then positioned with its pressure surface 72 centered at the selected pressure point, after which the free end portions of the belt 20 are drawn toward each other to apply desired tension to the belt 20 in the directions indicated by the directional arrows in FIGS. 7 and 8.

Application of tension to the compression belt 20 in the directions indicated by the directional arrows in FIGS. 7 and 8 causes the cruciform slot 62 to open as shown in FIGS. 6 and 7 thereby defining a socket receiving the parti-spherical head portion 68 of the compression element 22. Thus, the compression belt 20 cooperates with the compression element 22 to generally form a ball and socket or universal joint therebetween. Since the compression belt 20 is carried by the restraining member 12 which is secured in fixed position to the patient there is no direct connection between the compression belt and the patient. However, any slight relative movement which may occur between the belt 20 and the compression element 22 resulting from movement of the patient P will be substantially absorbed by the aforedescribed ball and socket joint formed by cooperation of the compression strap 20 and the compression element 22, so that a slight shifting movement of the strap 20 relative to the compression element 22 will not result in a shifting of the compression element from the preselected pressure point.

A patient wearing the device 10 and in a supine position may move from one side to the other without serious risk of dislodging the pressure element.

I claim:

1. A femoral compression device comprising; restraining means for limiting hip flexion of a patient and including a substantially rigid restraining member and attaching means for securing said restraining member in a substantially fixed predetermined general position on the patient's body, and adjustable compressing means carried by said restraining means for applying and maintaining external pressure at a femoral artery or vein puncture site.

2. A femoral compression device as set forth in claim 1 wherein said adjustable compressing means comprises a compression strap having opposite end portions connected to said restraining member.

3. A femoral compression device as set forth in claim 2 wherein said adjustable compressing means includes a discrete compression element for positioning between said compression strap and said puncture site to bear upon the patient's body proximate the puncture site.

4. A femoral compression device as set forth in claim 3 wherein said discrete compression element has a head portion for cooperating in bearing engagement with said compression strap and a frustoconical portion axially converging from said head portion for bearing upon the patient's body.

5. A femoral compression device as set forth in claim 4 wherein said head portion comprises a parti-spherical portion disposed within a generally complementary socket formed by said compression strap.

6. A femoral compression device as set forth in claim 5 wherein said socket is formed by a slit in said compression strap when said compression strap is in bearing engagement with said compression element.

7. A femoral compression device as set forth in claim 6 wherein said slit comprises a cruciform slit.

8. A femoral compression device as set forth in claim 1 wherein said adjustable compressing means comprises a discrete compression element and a compressing device for engaging said discrete compression element and urging it toward said puncture site.

9. A femoral compression device as set forth in claim 8 including ball and socket means for providing universal engagement between said compressing device and said discrete compression element.

10. A femoral compression device as set forth in claim 1 wherein said restraining member is anatomically contoured.

11. A femoral compression device as set forth in claim 10 wherein said restraining member is further characterized as a molded shell.

12. A femoral compression device as set forth in claim 11 wherein said restraining member comprises plastic material.

13. A femoral compression device as set forth in claim 12 wherein said plastic material comprises polypropylene.

14. A femoral compression device as set forth in claim 1 wherein said attaching means comprises adjustable strap means connected to said restraining member.

15. A femoral compression device as set forth in claim 14 wherein said adjustable strap means comprises an upper strap assembly connected to an upper portion of said restraining member and cooperating with the restraining member to encircle the patient's body in the region of the pelvic brim.

16. A femoral compression device as set forth in claim 14 wherein said adjustable strap means comprises a plurality of straps including mating J-hook and loop fastening materials for joining portions of said straps in releasable connected engagement.

17. A femoral compression device as set forth in claim 16 wherein said straps are fabricated from said loop fastening material and carry patches of said mating J-hook material.

18. A femoral compression device comprising; restraining means for limiting flexion of a hip and including a substantially rigid restraining member for disposal in a fixed predetermined general position overlying a posterior portion of a patient's body generally to one side of the body mid line and extending from the region of the pelvic brim to mid-thigh, attaching means for securing said restraining means in said predetermined general position and including an upper strap connected to an upper portion of said restraining member and cooperating with the restraining member to encircle the patient's body in the region of the pelvic brim and a lower strap connected to a lower portion of said restraining member and cooperating with the restraining member to encircle the patient's thigh, and adjustable compressing means connected to said restraining means for applying external pressure at a femoral artery or vein puncture site.

19. A method for preventing patient post catheterization wound bleeding comprising the steps of securing a substantially rigid member in a generally fixed predetermined position to the patient's body limiting the patient's hip flexion, attaching to the rigid member an adjustable compressing means for applying external pressure at the wound site and adjusting the compressing means to apply external pressure to the patient's body at the wound site after the patient's hip flexion has been limited.

20. A femoral compression device comprising; restraining means for limiting hip flexion of a patient and including a substantially rigid restraining member and adjustable strap means connected to said restraining member for securing said restraining member in a substantially fixed predetermined general position on the patient's body and including a lower strap assembly connected to a lower portion of said restraining member and cooperating with the restraining member to encircle the patient's thigh and adjustable compressing means carried by said restraining means for applying and maintaining external pressure at a femoral artery or vein puncture site.

21. A femoral compression device as set forth in claim 20 wherein said adjustable strap means includes an upper strap assembly connected to an upper portion of said restraining member and cooperating with said restraining member to encircle the patient's body in the region of the pelvic brim.

22. A femoral compression device as set forth in claim 21 wherein said adjustable compressing means comprises an adjustable strap member, a compression member, and securing means for maintaining said compression member between said adjustable strap member and the puncture site to bear against the patient's body proximate the puncture site.

23. A femoral compression device as set forth in claim 22 wherein one of the members comprising said compression member and said adjustable strap member has an opening therethrough and a portion of the other of said members extends through said opening.

24. A femoral compression device as set forth in claim 23 wherein said one of the members comprises said adjustable strap member.

25. A method for preventing patient post catheterization wound bleeding comprising the steps of providing a substantially rigid restraining member, positioning the restraining member in a fixed predetermined general position overlying a posterior portion of a patient's body and extending from the region of the pelvic brim to mid-thigh, strapping an upper portion of the restraining member to the patient's body in the region of the pelvic brim and strapping a lower portion of the restraining member to the patients thigh at a location below the wound site, attaching to the restraining member an adjustable compressing means for applying external pressure at the wound site, and adjusting the compressing means applying external pressure at the wound site after limiting the patient's hip flexion.

26. A method for preventing patient post catheterization wound bleeding as set forth in claim 25 wherein the step of attaching is further characterized as attaching an adjustable strap to the restraining member and, positioning a discrete compression element between the adjustable strap and the wound site, and the step of adjusting comprises tightening the adjustable strap causing the compression element to apply external pressure at the wound site.

* * * * *

UNITED STATES PATENT AND TRADEMARK OFFICE
CERTIFICATE OF CORRECTION

PATENT NO. : 5,799,650
DATED : Sep. 1, 1998
INVENTOR(S) : Harris

It is certified that error appears in the above-identified patent and that said Letters Patent is hereby corrected as shown below:

col. 2, line 57, delete "and" and insert -- an --.

col. 3, line 21, after "edge" insert -- is --.

col. 4, line 12, delete "46" and insert -- 36 --.

Signed and Sealed this

Twenty-third Day of February, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO.   : 5,799,650
DATED        : September 1, 1998
INVENTOR(S)  : Scott M. Harris It is certified that error appears in the above-identified patent and that said Letters Patent is hereby corrected as shown below:

Column 8,
Line 17, after "site" insert -- thereby limiting the patient's hip flexion --.
Line 21, delete "applying" and substitute -- to apply --.

Signed and Sealed this

Sixteenth Day of July, 2002

Attest:

Attesting Officer

JAMES E. ROGAN
Director of the United States Patent and Trademark Office